United States Patent [19]

Köpke et al.

[11] Patent Number: 4,471,171

[45] Date of Patent: Sep. 11, 1984

[54] DIGITAL HEARING AID AND METHOD

[75] Inventors: Wolfgang Köpke; Peter Wiener; Rainer Maas; Albert Eggert; Gerd-Wolfgang Götze, all of Berlin, Fed. Rep. of Germany

[73] Assignee: Robert Bosch GmbH, Stuttgart, Fed. Rep. of Germany

[21] Appl. No.: 466,840

[22] Filed: Feb. 16, 1983

[30] Foreign Application Priority Data

Feb. 17, 1982 [DE] Fed. Rep. of Germany ....... 3205685

[51] Int. Cl.$^3$ ............................................. H04R 25/00
[52] U.S. Cl. ........................ 179/107 R; 179/107 FD; 381/68
[58] Field of Search .................... 179/107 R, 107 FD; 381/68

[56] References Cited

U.S. PATENT DOCUMENTS 4,025,721 5/1977 Graupe ........................ 179/107 FD
4,187,413 2/1980 Moser ............................. 179/107 R
4,425,481 1/1984 Mansgold et al. .................... 381/68

Primary Examiner—G. Z. Rubinson
Assistant Examiner—L. C. Schroeder
Attorney, Agent, or Firm—Frishauf, Holtz, Goodman & Woodward

[57] ABSTRACT

To match the operation of a digital hearing aid directly to user requirements, and to reprogram the hearing aid as the hearing aid and/or user response characteristics change, a digital data processing element (12) processing digitized audio signals is connected to a programmable memory such as an EEPROM or an EARAM which stores predetermined frequency vs. amplitude transfer functions in accordance with user requirements or preference and/or hearing aid operation. Additionally, a memory (ROM 17) is provided storing a test program which causes the digital processor to generate test frequencies or tones at varying amplitudes, so that the transfer function in the programmable memory (15) can be changed or modified by operation of a switch (19) which can be manually user-operated or automatically, for example by measuring stapedius reflexes. After setting or changing the transfer function in the programmable memory (15), the normal program of the digital data processor—which can be of standard construction—is engaged by switch-over by a user-controlled transfer switch (18).

12 Claims, 2 Drawing Figures

DIGITAL HEARING AID AND METHOD

The present invention relates to hearing aids, and more particularly to hearing aids in which the incoming audio signal to digitized, processed in accordance with a function which relates amplification to frequency, and then reconverting the digitized for presentation as an analog signal to an earphone or earplug.

BACKGROUND

Various types of digital hearing aids have been proposed. The audio input, sensed by a microphone, is digitized, for example in an analog/digital (A/D) converter. The digitized signals or data are then applied to a microprocessor, for processing therein in accordance with a predetermined transfer function. The transfer function is stored in a memory, for example a read-only memory (ROM). After conversion in accordance with the transfer function as determined by the structure, and programming of the ROM, the digitized signal is reconverted in a D/A converter to an analog signal, for application to an electro-acoustic transducer, such as an earphone or an earplug.

It is known that the hearing acuity, with respect to frequency and amplitude of hard-of-hearing persons changes with time. It is, therefore, necessary to test hearing of the person and, if necessary, to exchange the hearing aid for one which is matched to the particular correction requirements of the user.

THE INVENTION

It is an object to improve hearing aids of the foregoing type so that they can be matched, by the user her/himself to the hearing deficiencies, and corresponding correction requirements of the user.

Briefly, a memory, such as an ROM, is provided in which a test program is stored, for example commanding the digital data processing apparatus in the digital hearing aid to generate a series of test tones, at predetermined test frequencies, with increasing amplitude. When response is sensed by the user, with respect to any one of the test tones, the user either operates a response switch, or an automatic pressure-sensitive response element can be used, introduced into an ear of the user and providing a corresponding response output. The amplitude/frequency relationship is then used to modify the transfer function, for example by reprogramming an EEPROM (electronically erasable programmable read-only memory) or an equivalent EARAM (electronically addressable random access memory), which replaces the standard ROM is prior art hearing aids, which did not permit matching the hearing aid to actual user requirements, but rather relied on standard function suitable for a wide variety of people.

The ROM generates a test program only; the EEPROM or EARAM controls the transfer function—and does so in accordance with selected modification by modifiying or correcting the transfer function in accordance with actual user requirements. A transfer switch, transferring operation of the data processing apparatus from normal hearing aid use to test or reprogramming use, is preferably provided to permit the user to make any changes and adjustments, that is, matching the output amplitude, with respect to frequency, of the hearing aid to the user's requirements.

The hearing aid has the advantage that the user can test her/his hearing with respect to frequency and amplitude characteristics, and can match the hearing aid to any possible changes in hearing acuity with respect to the frequencies of the audio spectrum. It is also possible to match the hearing aid to provide an individually adapted amplification/frequency transfer function within the hearing aid itself, so that the hearing aid will be matched to the hearing acuity characteristics of the user.

Individual correction of the response of the hearing aid, by the user, is possible not only by subjective test of the user, but also by objective audiometry, particularly by using the Stapedius reflex test. The individual possibilities to change the transfer function of the hearing aid, particularly the amplifier-frequency response thereo, are improved if the correction is made by subjective audiometry, for example by generating, based on a test program, pure tones of varying frequencies, the amplitudes of which are evaluated, subjectively, by the user. A user-operated test switch can be provided to signal to the apparatus when the user has heard a particular frequency at a selected amplitude level. The apparatus, thus, can be used both for subjective as well as for objective testing of the hearing of the user, and then adjustment of the hearing aid to match the specific requirements of the particular user.

DRAWINGS

DETAILED DESCRIPTION

Figure 1:
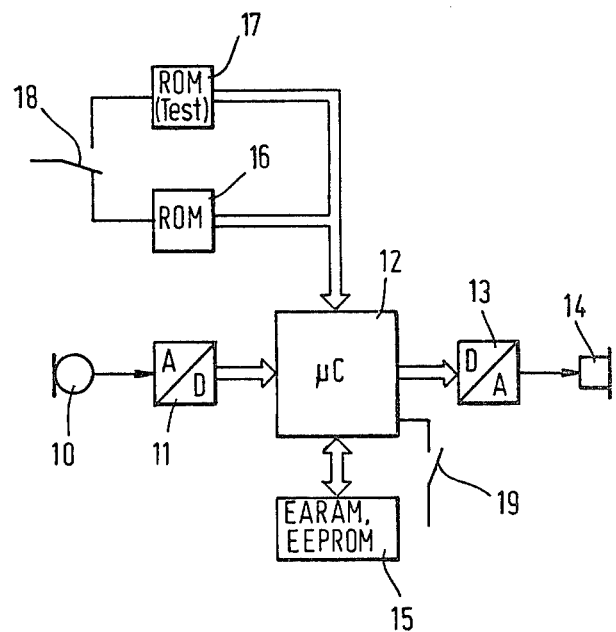
FIG. 1 is a schematic block diagram of an embodiment of the invention.

A microphone 10 is connected to an analog/digital (A/D) converter 11 to provide a digitized audio signal, derived from the microphone 10. The A/D converter 11 is connected to a data processing apparatus, typically a microprocessor 12, the outputs of which are connected to a digital/analog (D/A) converter 13. The D/A converter is connected to an earphone or earplug 14, forming an electro-audio transducer which projects audio waves into the ear of the user, for example a person having hearing problems.

A memory element 15 is connected to the microprocessor 12 by a two-way data bus.

In accordance with a feature of the invention, the memory 15 is a programmable memory, for example an electronically erasable programming read-only memory (EEPROM). Further, a program memory 16 is provided which retains therein the hearing program; a second ROM 17 is provided for a test program. The ROMs 16, 17 are connected by a data bus with the microprocessor 12. Transfer of the normal operating program of the microprocessor 12 to a test program is effected by a transfer switch 18 which is user-controlled. Of course, the ROMs 16, 17 can be incorporated within the same structure, for example a chip forming the microprocessor 12, or the respective programs retained within the ROM 16 and the ROM 17, can be placed in single ROM at respective addresses, the switch 18 then controlling addressing the respective addresses, for example by increasing or decrementing numbers representative of addresses.

The system further includes a switch 19, coupled to the microprocessor 12, to signal to the microprocessor when a predetermined amplitude/frequency relationship is obtained for which the memory 15 should be programmed or reprogrammed. Switch 19 can be user-operated—if the test program is to be based on user operation; or it may be automatically operated, for example include a pressure sensing operated switch, introducible into the ear of the user and coupled to the eardrum.

Figure 2:
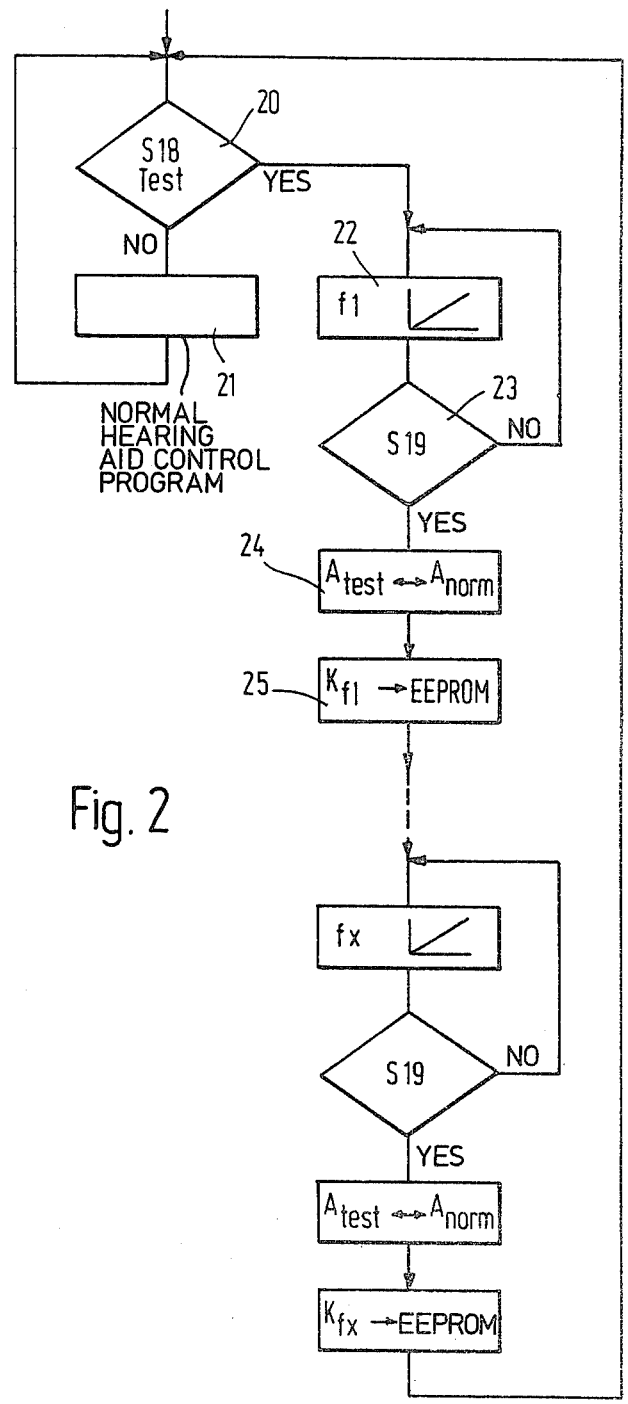
FIG. 2 is a flow diagram illustrating operation of the apparatus when correcting, or to change the frequency response of the hearing aid.

Operation, with reference to FIG. 2: The microprocessor—not shown in FIG. 2, and including, as well known, a clock which provides repetitive interrogation pulses, continuously interrogates the position of switch 18. If the switch 18—see block 20—is in normal position, that is, connecting the ROM 16, ROM 16 provides the normal data processing program to the microprocessor 12, in accordance with well known digital hearing aid control—see block 21.

In accordance with a feature of the invention, change-over of switch 18 to the ROM 17—tested by the test block 20—places the test program from ROM 17 in operation.

In the first test step, a first frequency $f_1$—see block 22—is connected through the microprocessor 12 and the D/A converter 13, to generate a tone in the audio transducer 14, the amplitude of which is increased continuously or in small steps. The microprocessor 12 then interrogates operation of the switch 19—block 23. The user of the apparatus is instructed to operate the switch 19 if subjective audiometry is to be carried out, as soon as the tone with the frequency $f_1$ is perceived. Upon operation of switch 19, microprocessor 12 compares if the amplitude $A_{test}$ corresponds to a normal amplitude $A_{norm}$ of a normally hearing person—see block 24. Depending on the deviation, for exmaple a higher amplitude requirement by the particular user at the frequency $f_1$, a correction factor $K_{f1}$ is applied to the memory 15—see block 25. This correction factor $K_{f1}$ determines, for the furture normal hearing program controlled by the ROM 16, upon subsequent change-over of switch 18—the transmission of all sounds having a frequency $f_1$ and, specifically, the amplification factor of the amplifier inherently contained in the hearing aid.

The sequence of steps testing for a frequency $f_1$ is repeated for subsequent frequencies, until the last, for example highest frequency $f_x$, to which the hearing aid can respond, and which is provided within the test program of ROM 17, has been tested, and a correction factor $K_{fx}$ is stored in the EEPROM 15. The EEPROM 15, then, will have a new transfer function stored therein, which relates the correction factors $K_{f1} \ldots K_{fx}$ to the respective amplitudes, or amplification factors of the amplifier in the hearing aid.

The test system described used subjective audiometry as the criterion for generation of the transfer function within the memory 15. Objective audiometry by automatic Stapedius reflex measurement is also, and preferred for some users. For automatic measurement, a pressure sensor is introduced in the ear, in pressure transfer relationship to the eardrum of the hearing-impaired user, the pressure sensor including the switch 19 which, now, rather than being subjectively operated by the user, will respond, objectively, to pressure variations signalled from the eardrum. The correction test program then will run as desribed above, the only difference being that the determination of $A_{test}$ will be determined by response of the pressure sensor at a predetermined pressure amplitude signalled from the eardrum of the user.

Various changes and modifications may be made within the scope of the inventive concept.

Hearing aids have been described in the literature; their construction, and the programming of a microprocessor 12 by an ROM, such as the ROM 16, to control the program of the microprocessor, and a memory—albeit a fixed memory—to control the transfer function of the digital processor 12 are also known. Reference is made to the following:

U.S. Pat. No. 4,187,413 (HEARING AID WITH DIGITAL PROCESSING)

Deutsche Offenlegungsschrift No. 27 35 024 (AUDIOMETER WITH DIGITALLY GENERATED TONES)

U.S. Pat. No. 3,808,354 (COMPUTER CONTROLLED METHOD AND SYSTEM AUDIOMETRIC SCREENING)

Suitable units for the respective stages are:

Pos. 15 EEPROM 2816 (INTEL)
Pos. 16 ROM 2308 (INTEL)
Pos. 17 ROM 2308 (INTEL)
Pos. 12 Signal processor 2920 (INTEL)
Pos. 11 A/D converter HI 5712 (Harris Semiconductor)
Pos. 13 D/A converter AD 7111 (Analog Devices)

We claim:

1. Hearing aid having
a microphone (10) to receive audio input;
an analog/digital converter (11) connected to the microphone and digitizing received audio input and providing audio digital data;
a digital/analog converter (13) receiving digital audio data and converting the digital data into analog audio output;
an earphone or earplug (14) connected to receive the analog audio output from the digital/analog converter;
means (15) storing a predetermined frequency/analog transfer function; and
a digital data processor (12) connected to said storage means (15) for receiving said function, and processing the digital data received from the analog/digital converter (11), in digital form, for obtaining derived data in which the received data are amplified in accordance with a predetermined frequency vs. amplitude transfer function derived from said storage means;
and comprising, in accordance with the invention,
correction means (15, 19, 17, 18, 12) connected to and selectively (18, 19) controlling the storage means (15) which controls the transfer function of the digital data processor including
means (17) for generating a series of test data representative of standard test tones or frequencies, for transmission to the earphone (14);
said storage means (15) having the characteristic of being reprogrammable to change the frequency vs. amplitude transfer function stored therein;
and user reaction controlled switch means (19) connected to the storage means (15) to modify the frequency vs. amplitude transfer function in accordance with a preference of the user.

2. Hearing aid according to claim 1, including a control memory (16) controlling the operation of said digital data processor (12);
and wherein the correction means includes a test memory (17) storing data controlling the digital data processor to provide a test tone or test program;

and user-operated selective switch means (18, 19) selectively operable to place either the control memory or the test memory in operative connection with said digital data processor.

3. Hearing aid according to claim 1, wherein the user reaction controlled switch means (19) comprises a Stapedius reflex operated switch.

4. Hearing aid according to claim 3, wherein said switch comprises a pressure switch adapted for association with the eardrum of the user.

5. Hearing aid according to claim 1, wherein the user reaction controlled switch means (19) comprises a manually controlled user-operable switch.

6. Hearing aid according to claim 2, wherein the digital data processor (12) includes means generating a plurality of tones of varying frequency connectable to said earphone or earplug under control of said test program, said tones varying in amplitude;

and wherein said user reaction controlled switch means (19) is connected to said reporgrammable storage means (15) to store a frequency vs. amplitude transfer function under control of the user upon operation of said reaction controlled switch means (19).

7. Hearing aid according to claim 6, wherein the user reaction controlled switch means (19) comprises a manually controlled user-operable switch.

8. Hearing aid according to claim 1, wherein said reprogrammable storage means (15) comprises an electronically erasable programmable read-only memory (EEPROM) (15).

9. Hearing aid according to claim 1, wherein said reprogrammable storage means comprises an electronically addressable random access memory (EARAM).

10. Hearing aid according to claim 2, wherein said reprogrammable storage means (15) comprises at least one of: an electronically erasable programmable read-only memory (EEPROM); an electronically addressable random access memory (EARAM).

11. Hearing aid according to claim 6, wherein said reprogrammable storage means (15) comprises at least one of: an electronically erasable programmable read-only memory (EEPROM); an electronically addressable random access memory (EARAM).

12. Method of matching the response of a hearing aid to individual requirements of a user, comprising
providing a digital data processor (12) processing digital audio data and providing an output for conversion to analog audio signals, for application to an ear of the user and comprising the steps of
generating, within the earphone, a series of test tones of respectively different frequency, and of varying amplitude;
providing a user-reaction controlled switch (19);
providing a control memory (17) controlling generation of said frequencies at the varying amplitudes;
connecting said control memory, selectively, under control of the user, to the digital data processor to cause the digital data processor to provide said respective frequencies of varying amplitude, and storing the frequency/amplitude relationship in a reprogrammable memory (15) in accordance with the preference of the user based on reaction of the user to specific frequencies at specific amplitudes;
and then connecting a second control memory (16) to the digital data processor for processing of random received audio signals therein in accordance with the frequency vs. amplitude transfer function stored in the programmable memory based on the reaction and the preference of the user.

* * * * *